(12) United States Patent
Ebringer

(10) Patent No.: US 6,849,418 B1
(45) Date of Patent: Feb. 1, 2005

(54) DIAGNOSIS OF SPONGIFORM OR DE-MYELINATING DISEASE

(75) Inventor: Alan Ebringer, Ealing (GB)

(73) Assignee: King's College London (GB)

( * ) Notice: Subject to any disclaimer, the term of this patent is extended or adjusted under 35 U.S.C. 154(b) by 0 days.

(21) Appl. No.: 09/646,579

(22) PCT Filed: Mar. 19, 1999

(86) PCT No.: PCT/GB99/00876

§ 371 (c)(1),
(2), (4) Date: Dec. 27, 2000

(87) PCT Pub. No.: WO99/47932

PCT Pub. Date: Sep. 23, 1999

(30) Foreign Application Priority Data

Mar. 19, 1998 (GB) .............................................. 9805913

(51) Int. Cl.$^7$ ........................ G01N 33/554; C12Q 1/70; A61K 49/00
(52) U.S. Cl. .................... 435/7.32; 424/9.1; 424/130.1; 424/139.1; 435/5
(58) Field of Search ............................... 424/9.1, 130.1, 424/139.1; 435/5, 7.32

(56) References Cited

U.S. PATENT DOCUMENTS 5,565,186 A * 10/1996 Prusiner et al.

OTHER PUBLICATIONS

Harnet et al. (J Bacteriol 1990 172(2) pp. 956–966).*
Marchalonis et al. (Antibody as a Tool–The Applications of Immunochemistry, Chapter 2,3,13,14, John Wiley and Sons, UK 1982).*

* cited by examiner

Primary Examiner—Rodney P Swartz
(74) Attorney, Agent, or Firm—Joseph T. Leone, Esq.; DeWitt Ross & Stevens S.C.

(57) ABSTRACT

Disclosed are a method and a corresponding kit for detecting multiple sclerosis, Creutzfeld-Jakob disease, and/or spongiform encephalopathy in mammals. The method includes the step of testing a biological sample obtained from the mammal for IgA antibodies which bind to *Acinetobacter* species. An elevated level of such IgA antibodies is indicative of multiple sclerosis, Creutzfeld-Jakob disease, and/or spongiform encephalopathy in the mammal tested. The test kit contains an antigen specific for IgA antibodies that are reactive with *Acinetobacter* species.

9 Claims, 2 Drawing Sheets

Figure 1:
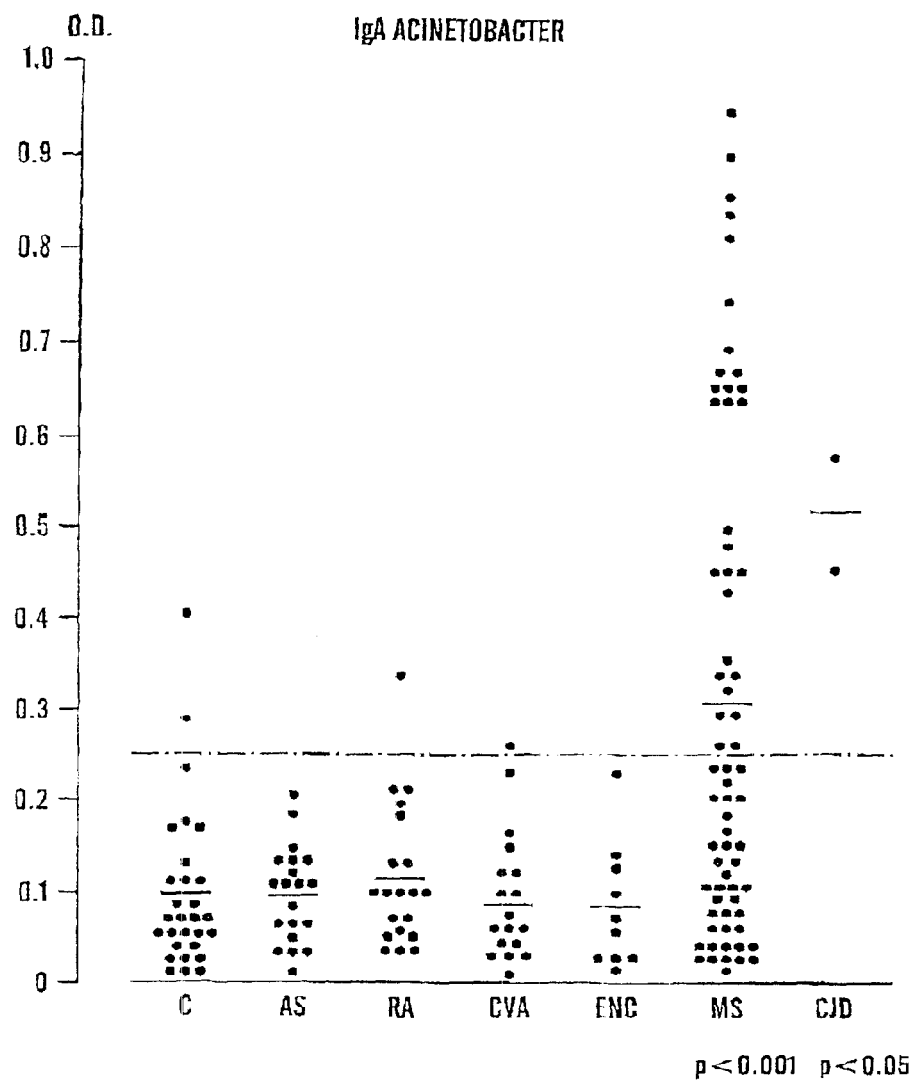

LEGEND: IgA ANTIBODIES TO ACINETOBACTER BACTERIA, MEASURED BY ELISA IN HEALTHY CONTROLS (C) AND PATIENTS WITH ANKYLOSING SPONDYLITIS (AS), RHEUMATOID ARTHRITIS (RA), CEREBRO-VASCULAR ACCIDENTS (CVA), VIRAL ENCEPHALITIS (ENC), MULTIPLE SCLEROSIS (MS) AND CREUTZFELDT-JAKOB DISEASE (CJD). (p-VALUES INDICATE SIGNIFICANCE COMPARED TO CONTROLS)

SEQUENCE LISTING

```
<160> NUMBER OF SEQ ID NOS: 2

<210> SEQ ID NO 1
<211> LENGTH: 8
<212> TYPE: PRT
<213> ORGANISM: Acinetobacter calcoaceticus

<400> SEQUENCE: 1

Arg Phe Ser Ala Trp Gly Ala Glu
1               5

<210> SEQ ID NO 2
<211> LENGTH: 9
<212> TYPE: PRT
<213> ORGANISM: Acinetobacter calcoaceticus

<400> SEQUENCE: 2

Ile Ser Arg Phe Ala Trp Gly Glu Val
1               5
```

DIAGNOSIS OF SPONGIFORM OR DE-MYELINATING DISEASE

Priority is hereby claimed to PCT application Ser. No. PCT/GB99/00876, filed 19 Mar. 1999, which application claims priority to Great Britain Serial No. GB 9805913.2, filed 19 Mar. 1998; additionally this is a continuation-in-part of co-pending application Ser. No. 09/269,607, filed 26 Jul. 1999 (and incorporated herein by reference), which application claims priority to PCT application Ser. No. PCT/GB97/02667.

This invention relates to the diagnosis of de-myelinating diseases and spongiform encephalopathies in animals and humans.

In our copending application WO 98/13694 we have disclosed a new diagnostic test for spongiform encephalopathies and other de-myelinating conditions in mammals. The test disclosed in our prior application is based on a model of the genesis of this pathological state which is applicable to the various forms in which it is manifest in humans and animals. In relation to the bovine spongiform disease this model provides an alternative to the current theory based on the formation of prions. Briefly, this new model is based on the phenomenon of molecular mimicry according to which mammals exposed to certain bacteria having peptide sequences which mimic myelin peptides experience an auto-immune reaction. In our prior application we indicated that human de-myelinating diseases were also open to the same explanation according to our new model disclosed therein.

According to the present invention, a method for detecting a de-myelinating disease or spongiform encephalopathy in mammals comprises testing a biological sample obtained from the mammal for IgA antibodies indicative of infection by an *Acinetobacter* species. We believe that infective micro-organisms of these species present to the mammal an antigen which exhibits molecular mimicry with the myelin of the mammal. The phenomenon of molecular mimicry has been explained in our above-mentioned prior application WO 98/13694, the contents of which are hereby incorporated by reference.

We have now confirmed the presence of elevated levels of certain antibodies in human sera of patients suffering from multiple sclerosis (MS). These are the IgA antibodies to *Acinetobacter* species e.g. *Acinetobacter calcoaceticus*, the same organisms for which antibodies were previously found in BSE sera. Similar results have been obtained for Creutzfeld-Jakob disease (CJD). Tests for antibodies in sera from patients who had died of CJD also show increased levels, this being especially marked for the IgA antibody sub-class. The same IgA specificity also applies to bovine sera used for the tests described in our above-mentioned copending application.

It is clear that humans suffering from MS and CJD and cows suffering from BSE all have very significantly raised levels of *Acinetobacter calcoaceticus* IgA antibodies in their blood. Tests for such antibodies in sera from living subjects at an early stage make it possible to identify those liable to develop these diseases. The present invention opens up the opportunity of early treatment of these infections e.g. by use of an appropriate antibiotic to prevent further auto-immune attack on the subjects' own myelin.

As also indicated in our application WO 98/13694, *Acinetobacter calcoaceticus* is one species of *Acinetobacter* which provides an antigen which stimulates the formation of antibodies which cross-react with the mammalian myelin. Antibodies have been demonstrated to react with several strains of this species including 17905, AC606, SP13TV, 105/85, and 11171. These are in the Reference Centre for *Acinetobacter* species held by Dr Kevin Towner, Public Health Laboratory, University of Nottingham, U.K.

In carrying out the present invention, the test is for antibodies which bind to an epitope present in or derived from the *Acinetobacter* species. The antigen used in the test may be the whole organism or at least one prepared peptide sequence corresponding to an *Acinetobacter* epitope. Alternatively, peptide sequences may be used which have minor variations in amino-acid sequence from the above-mentioned epitopes or prepared peptides but are conformationally sufficiently similar to them that they also bind to the relevant antibodies. For example, peptides having the sequence RFSAWGAE (SEQ. ID NO: 1) or ISRFAWGEV (SEQ. ID NO: 2) may be used.

A test kit for use according to the invention therefore contains at least one test antigen as just indicated. In order to reveal IgA antibodies the kit also contains a secondary antibody against the human, bovine, or other mammalian IgA.

As indicated in WO 98/13694, antibodies are assayed and a positive result is indicated by levels of antibodies at least about two standard deviations above that of control samples.

In view of the greater specificity of the IgA antibodies in the immune response it may be concluded that the mechanism of infection with *Acinetobacter* is via the mucous membranes of the body, the primary sites being the gut or the nasal passages. Since a further correlation has been observed between MS sufferers and patients with major sinus infections, it is probable that the nasal passages

EXAMPLE

The assay for the above mentioned organisms is described in our co-pending application mentioned above. The improved method used herein is as follows:

Elisa Test

1) Aliquots of 200 ul of the diluted suspension of *Acinetobacter calcoaceticus* (NCIMB 10694, Aberdeen) grown in nutrient broth are absorbed onto 96 well flat bottomed rigid polystyrene microtitre plates overnight at 4° C.
2) The plates are then washed 3 times with phosphate buffered saline (PBS), 0.1% (v/v) Tween 20.
3) Aliquots of 200 $\mu$l of blocking solution (0.2% w/v ovalbumin, 0.1% v/v Tween 200 in PBS is added to each well and incubated for one hour at 37° C.
4) The plates are then washed 3 times with PBS.Tween 20.
5) Aliquots of 200 $\mu$l serum samples (test or control) diluted 1/200 in PBS. Tween 20 is added and incubated for 2 hours at 37° C.
6. The plates are then washed 3 times with PBS.Tween 20.
7) Aliquots of 200 $\mu$l of peroxidase conjugated rabbit anti-human IgA or rabbit anti-cow Iga, diluted 1/4000 (cow) (or 1/500 for human) with PBS.Tween 20 are added and incubated for 2 hours at 37° C.
8) The plates are then washed 3 times with PBS.Tween 20.
9) The development of the colormetric assay takes place at room temperature for 20 minutes, after the addition of 200 $\mu$l per well of 0.5 mg/ml (2,2'-azinobis(3-ethylbenzthiazoline-6-sulphonic acid) in citrate/phosphate buffer, pH 4.1, containing 0.98 mM hydrogen peroxide.
10) the reaction is then stopped with 100 $\mu$l of 2 mg/ml sodium fluoride and optical densities measured at a wavelength of 630 nm with a micro-ELISA plate reader.

Figure 2:
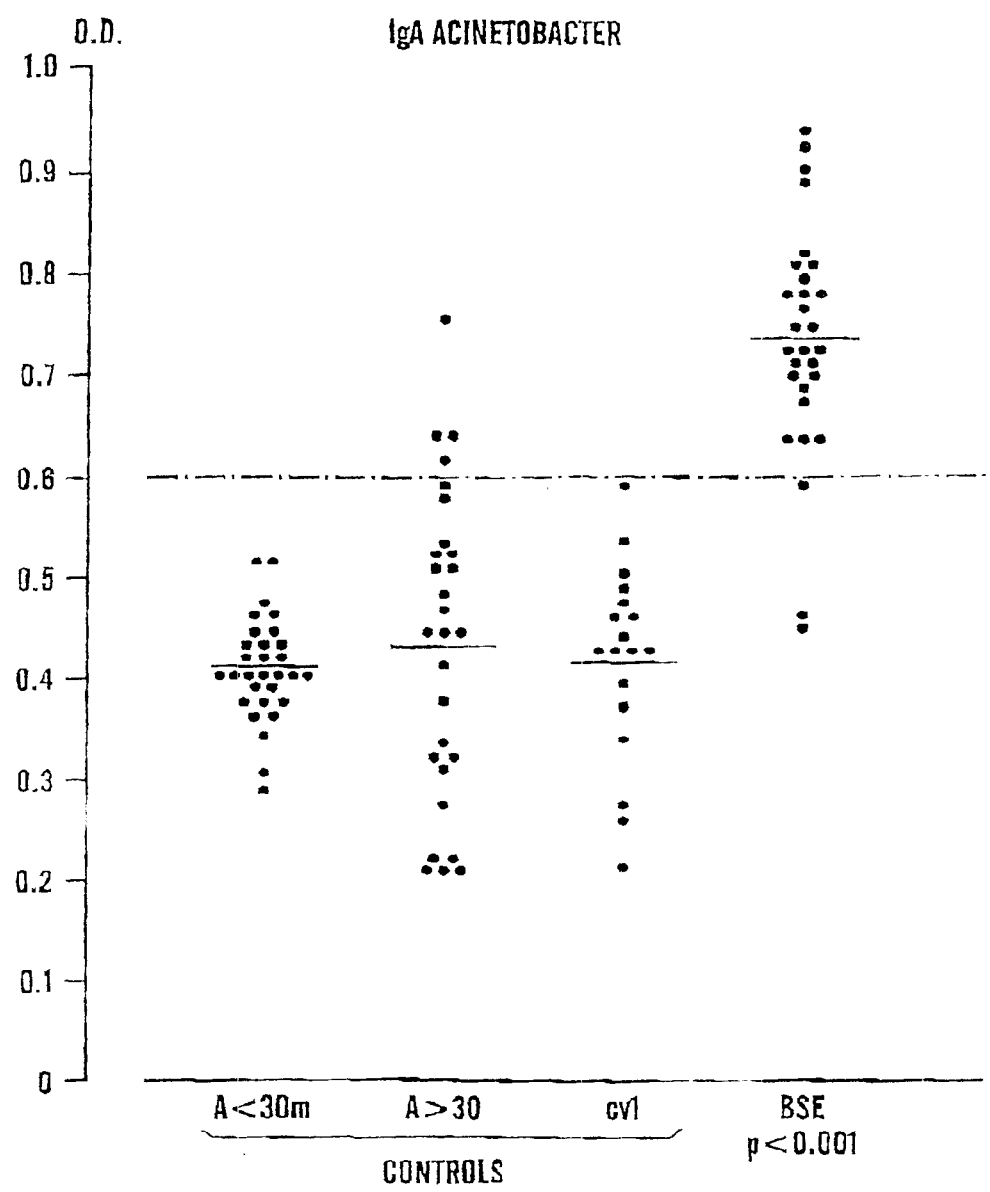

Results for MS and CJD are shown in the attached FIG. 1 and those for BSE are shown in FIG. 2. These give the titres of IGA *Acinetobacter* antibodies in MS and CJD sera, BSE sera, and control sera. The dashed line represents the 95% confidence limits of the controls.

What is claimed is:

1. A method for detecting multiple sclerosis, Creutzfeld-Jakob disease, or spongiform encephalopathy in mammals which comprises testing a biological sample obtained from the mammal for IgA antibodies which bind to *Acinetobacter* species.

2. A method according to claim 1, in which the *Acinetobacter* is one which presents to the mammal an antigen which exhibits molecular mimicry with the myelin of the mammal.

3. A method according to claim 1, in which the antibodies are indicative of prior exposure to *Acinetobacter calcoaceticus*.

4. A method according to claim 1, in which the disease tested for is bovine spongiform encephalopathy.

5. A method according to claim 1, in which the disease tested for is multiple sclerosis in humans.

6. A method according to claim 1, in which the disease tested for is Creutzfeld-Jacob disease in humans.

7. A method according to claim 1, in which antibodies are assayed and a positive result is indicated by levels of antibodies at least about two standard deviations above that of control samples.

8. A test kit for detecting multiple sclerosis, Creutzfeld-Jakob disease, or spongiform encephalopathy in mammals, the test kit comprising whole *Acinetobacter* organism and a secondary antibody against human, bovine, or other mammalian IgA.

9. A method according to claim 1, in which antibodies are assayed and a positive result is indicated by levels of antibodies significantly higher than that of control samples.

* * * * *